United States Patent
Stuk et al.

(10) Patent No.: US 9,926,327 B2
(45) Date of Patent: Mar. 27, 2018

(54) PROCESS FOR PREPARING 7H-PYRROLO[2,3-D]PYRIMIDINE COMPOUNDS

(71) Applicant: Zoetis Services LLC, Parsippany, NJ (US)

(72) Inventors: Timothy Lee Stuk, Mattawan, MI (US); Denis Billen, Kalamazoo, MI (US); Valerie Sue Westrick, Grandville, MI (US); Vageesha Warnajith Liyana Gunawardana, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 15/426,292

(22) Filed: Feb. 7, 2017

(65) Prior Publication Data

US 2017/0233397 A1    Aug. 17, 2017

Related U.S. Application Data

(60) Provisional application No. 62/375,040, filed on Aug. 15, 2016, provisional application No. 62/295,739, filed on Feb. 16, 2016.

(51) Int. Cl.
| | |
|---|---|
| C07D 487/04 | (2006.01) |
| C07C 303/22 | (2006.01) |
| C07C 303/32 | (2006.01) |
| C07C 309/19 | (2006.01) |
| C07C 309/24 | (2006.01) |
| C07C 309/30 | (2006.01) |

(52) U.S. Cl.
CPC .......... *C07D 487/04* (2013.01); *C07C 303/22* (2013.01); *C07C 303/32* (2013.01); *C07C 309/19* (2013.01); *C07C 309/24* (2013.01); *C07C 309/30* (2013.01)

(58) Field of Classification Search
CPC .................................................... C07D 487/04
See application file for complete search history.

(56) References Cited

U.S. PATENT DOCUMENTS

| | | | |
|---|---|---|---|
| 6,610,847 | B2 | 8/2003 | Blumenkopf et al. |
| 8,133,899 | B2 | 3/2012 | Mitton-Fry et al. |

*Primary Examiner* — Bruck Kifle
(74) *Attorney, Agent, or Firm* — Paul M. Misiak

(57) ABSTRACT

Described herein are improved processes for the preparation of the 7H-pyrrolo[2,3-d]pyrimidine compound, N-methyl-1-{trans-4-[methyl(7H-pyrrolo[2,3-d]pyrimidin-4-yl)amino]cyclohexyl}-methanesulfonamide, intermediates thereof, and veterinary acceptable salts thereof.

20 Claims, 4 Drawing Sheets

PROCESS FOR PREPARING 7H-PYRROLO[2,3-D]PYRIMIDINE COMPOUNDS

CROSS REFERENCE TO RELATED APPLICATIONS

This application claims the benefit of U.S. Provisional Application Nos. 62/295,739 and 62/375,040, filed Feb. 16, 2016 and Aug. 15, 2016, respectively. The prior applications are incorporated herein by reference in their entirety.

FIELD OF THE INVENTION

Described herein is an improved process for preparing a 7H-pyrrolo[2,3-d]pyrimidine compound, particularly, N-methyl-1-{trans-4-[methyl(7H-pyrrolo[2,3-d]pyrimidin-4-yl)amino]cyclohexyl}-methanesulfonamide, intermediates thereof, and veterinary acceptable salts thereof.

BACKGROUND OF THE INVENTION

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dis-regulation or de-regulation, as well as over- or under-production of growth factors or cytokines has been implicated in many diseases, including but not limited to cancer, allergies, asthma and other respiratory diseases, autoimmune diseases, and inflammatory diseases. Inappropriate kinase activity triggers a variety of biological cellular responses relating to cell growth, cell differentiation, survival, apoptosis, mitogenesis, cell cycle control, and cell mobility implicated in the aforementioned and related diseases.

Thus, protein kinases have emerged as an important class of enzymes as targets for therapeutic intervention. In particular, the JAK family of cellular protein tyrosine kinases (JAK-1, JAK-2, JAK-3, and Tyk-2) play a central role in cytokine signaling (Kisseleva et al, Gene, 2002, 285, 1; Yamaoka et al. Genome Biology 2004, 5, 253)). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression. Numerous cytokines are known to activate the JAK family.

Processes for preparing JAK inhibitors have been previously described in U.S. Pat. No. 6,610,847. Processes for preparing the specific JAK inhibitor, N-methyl-1-{trans-4-[methyl(7H-pyrrolo[2,3-d]pyrimidin-4-yl)amino]cyclohexyl}-methanesulfonamide was described in U.S. Pat. No. 8,133,899. The current synthetic process for preparing the Formula 1 compound is composed of at least 10 synthetic steps including 7 isolations. The improved synthetic route described herein is composed of only 6 synthetic steps and 4 isolations. Accordingly, there remains a need for alternative processes to prepare the JAK inhibitor, N-methyl-1-{trans-4-[methyl(7H-pyrrolo[2,3-d]pyrimidin-4-yl)amino]cyclohexyl}-methanesulfonamide, particularly one that can reduce processing time and cost.

SUMMARY OF THE INVENTION

The present invention provides an improved process for manufacturing a 7H-pyrrolo[2,3-d]pyrimidine compound of Formula 1,

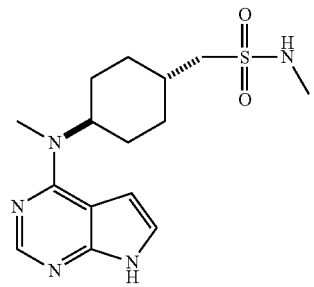

(1)

N-methyl-1-{trans-4-[methyl(7H-pyrrolo[2,3-d]pyrimidin-4-yl)amino]cyclohexyl}-methanesulfonamide, or a veterinary acceptable salt thereof, and intermediates thereof.

One aspect of the invention, is a process for preparing (4-(methylamino)phenyl)-methanesulfonic acid, Intermediate B,

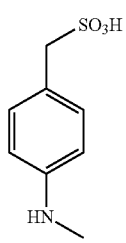

(B)

comprising the steps of reacting Intermediate a1

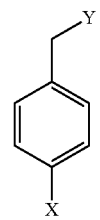

(a1)

wherein X is bromine or iodine and Y is Cl, Br, I, O-tosyl, O-mesyl, or O-triflate, (or any functional group that is susceptible to nucleophilic displacement by a sulfite salt) with a sulfite salt ($MSO_3$, wherein M is Na, K, or Ca) in water or an aqueous organic solvent at a temperature of about 50° C. to reflux will yield the resultant sulfite salt, Intermediate a2.

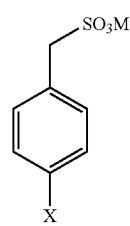

(a2)

Preferably, the variables X and Y for Intermediate a1 are both Br (i.e., 4-bromobenzylbromide) and M is Na or K for Intermediate a2. In one aspect, the sulfite salt is sodium sulfite. In another aspect, the sulfite salt is potassium sulfite. Use of sodium sulfite in the presence of 4-bromobenzylbromide in the reaction defined above yields Intermediate A, sodium (4-bromophenyl)methane-sulfonate (i.e., Intermediate a2 wherein X is Br and M is Na, shown below). The aqueous organic solvent for this sulfite conversion is about 1% to about 50% organic solvent. A preferred amount of organic solvent is about 10% to about 30%. A more preferred amount of organic solvent is about 15%. A preferred organic solvent is acetonitrile. In another aspect of the invention, the organic solvent can also be selected from acetone, water-miscible alcohols, and water-miscible ethers. The reaction temperature is about 50° C. to reflux. The preferred reaction temperature is about 80° C. for about 4 hours, after which the reactants are cooled to about 10° C. The resultant sodium sulfonate solids, Intermediate A,

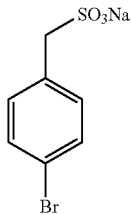

(A)

are isolated by filtration. Intermediate A is subsequently reacted with copper or a copper salt catalyst in an aqueous methylamine solution at a temperature of at least about 50° C. The reaction is cooled and water added. The pH is adjusted to about 3.2 with an acid. The resulting slurry is cooled further and the resultant solids, Intermediate B, are isolated. The preferred reaction temperature of at least about 50° C. is about 90° C. and the reaction time is about 16 hours. The copper catalyst can be Cu(0) or a Cu(1) salt. The preferred copper catalyst is a Cu(1) salt. The more preferred copper catalyst is CuBr. The catalyst loading can be any amount greater than about 0.25 mol %. The preferred copper catalyst load is about 2 mol %. The aqueous methylamine is at a concentration of about 5% to about 40% methylamine. The preferred amount of methylamine for the reaction is about 10% to about 25% methylamine. The more preferred amount of methylamine for the reaction is about 17% methylamine. The reaction is cooled from about 90° C. to about 65° C. A solution of citric acid is added to the reactants and stirred for about 20 minutes to remove copper residuals. Water is added and the pH adjusted to about 3.2 with concentrated aqueous hydrochloric acid. The resulting slurry is cooled to about 15° C. and the resultant solids, Intermediate B, are isolated by filtration, and washed with water.

In another aspect of the invention, is a process for preparing (4-(methylamino)phenyl)-methanesulfonic acid, Intermediate B,

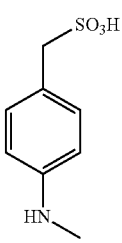

(B)

comprising the steps of reacting 4-bromobenzylbromide with sodium sulfite in water or an aqueous organic solvent comprising about 15% acetonitrile at a temperature of about 80° C. for about 4 hours, after which the reactants are cooled to about 10° C. The resultant sodium sulfonate solids, Intermediate A, are isolated by filtration and reacted with a 2 mol % CuBr catalyst in an aqueous organic solvent comprising about 17% methylamine at a temperature of about 90° C. for about 16 hours. The reaction is cooled to about 65° C. A solution of citric acid is added and the reactants stirred for about 20 minutes to remove copper residuals, after which water is added. The pH is adjusted to about 3.2 with concentrated aqueous HCl. The resulting slurry is cooled to about 15° C. and the resultant solids, Intermediate B, are isolated by filtration, and washed with water.

Another aspect of the invention is the preparation of the trans-geometric achiral isomer, trans-4-((methylamino)cyclohexyl)methanesulfonic acid, Intermediate C,

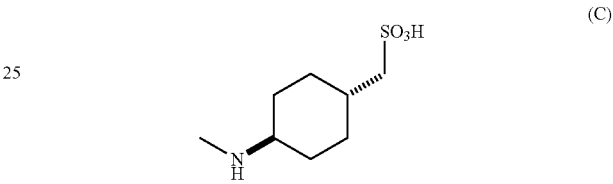

(C)

by the catalytic hydrogenation of Intermediate B at an elevated temperature. Intermediate B is reacted in an aqueous organic solvent with hydrogen in the presence of a catalyst at a temperature of about 40° C. to about 100° C. for about 12 hours to about 20 hours. A preferred reaction temperature is about 50° C. to about 80° C. for about 14 hours to about 18 hours. A more preferred reaction temperature is about 70° C. for about 16 hours. Hydrogenation can be accomplished with pressurized hydrogen gas or under other hydrogen transfer conditions, for example, using formic acid or formic acid salts as the hydrogen source. The preferred source of hydrogen is hydrogen gas that is under pressure at about 20 psi to about 70 psi. The preferred pressure is about 30 psi. The catalyst is a reactive metal catalyst, for example, palladium (e.g., Pd(0); or Pd(II); palladium hydroxide (Pd(OH)$_2$)), ruthenium (Rh), platinum (Pt and PtO$_2$)), and the like. The preferred catalyst is palladium. The preferred palladium catalyst is Pd(0) on carbon. The preferred loading of Pd(0) is about 10% on carbon. The aqueous organic solvent is water and methanol. The preferred amount of methanol is about 25%. The reaction yields both the trans (70%) and cis (30%) geometric achiral isomers of (4-(methylamino)cyclohexyl)methanesulfonic acid in solution. To purify the trans/cis slurry to obtain the trans-isomer, the reactant volume is concentrated and an alcohol is added to the aqueous slurry. The preferred alcohol is methanol, ethanol, or isopropanol. The more preferred alcohol is ethanol. The aqueous ethanol solution is about 10% to about 20% water. Preferably, the aqueous ethanol solution is about 16% to about 17% water. The slurry is heated to about 45° C. and then cooled to about 0° C. over a period of about 4 hours. The solids (Intermediate C) are isolated by filtration and washed with an alcohol, preferably ethanol.

In another aspect of the invention is a process for preparing Intermediate C, comprising the steps of:

a) reacting 4-bromobenzylbromide with a sodium sulfite salt in water or an aqueous solvent comprising about 10% to about 30% acetonitrile at about 80° C., and isolating the solids, Intermediate A, by filtration;

b) reacting the solids, Intermediate A, in aqueous methylamine that is about 10% to about 25% methylamine and a CuBr catalyst at a temperature of at least 50° C. for about 16 hours, then cooling the reactants to about 65° C., adding citric acid to remove residual copper, adding water and adjusting the pH to 3.2 with concentrated HCl, cooling the reaction to about 15° C., and isolating the solids, Intermediate B, by filtration;

c) reacting the solids, Intermediate B, in an aqueous organic solvent containing about 25% methanol with a palladium catalyst and hydrogen at about 50° C. to about 80° C. for about 14 hours to about 18 hours; and d) concentrating the volume from the previous reaction, adding an alcohol and heating to about 45° C., then cooling the reaction to about 0° C. over about 4 hours, and isolating the solids, Intermediate C, by filtration, and washing with an alcohol.

In yet another aspect of the invention is a process for preparing Intermediate C, comprising the steps of:

a) reacting 4-bromobenzylbromide with a sodium sulfite salt in an aqueous organic solvent comprising about 15% acetonitrile at about 80° C. for about 4 hours and then cooling the reaction to about 10° C., and then isolating the solids, Intermediate A, by filtration;

b) reacting the solids, Intermediate A, with aqueous methylamine that is about 17% methylamine and a CuBr catalyst that is about 2 mol % at about 90° C. for about 16 hours, then cooling the reactants to about 65° C. and adding citric acid to remove residual copper;

c) adding water and adjusting the pH to about 3.2 with concentrated aqueous hydrochloric acid, cooling the reaction to about 15° C., and isolating the solids, Intermediate B, by filtration;

d) reacting the solids, Intermediate B, in an aqueous organic solvent containing about 25% methanol with hydrogen gas at about 20 psi to about 70 psi and a Pd(0) catalyst at a temperature of about 70° C. for about 16 hours;

e) concentrating the reactant volume and adding ethanol;

f) heating the reactants to about 45° C. and then cooling to about 0° C. over about 4 hours; and g) isolating the solids, Intermediate C, by filtration, and washing the solids with ethanol.

In yet another aspect of the invention is the process for preparing the compound, Intermediate C, comprising the steps of:

a) reacting Intermediate B in an aqueous organic solvent at about 70° C. for about 16 hours with hydrogen gas at about 30 psi with a Pd(0) catalyst that is about 10% loading on carbon, wherein the aqueous organic solvent is about 25% methanol in water;

b) concentrating the reactant volume and adding ethanol;

c) heating the reactants to about 45° C. and then cooling to about 0° C. over about 4 hours; and d) isolating the solids, Intermediate C, by filtration, and washing the solids with ethanol.

In another aspect of the invention is the process for preparing trans-4-(methyl(7H-pyrrolo[2,3-d]pyrimidin-4-yl)amino)cyclohexyl)methane sulfonic acid, potassium salt, Intermediate E,

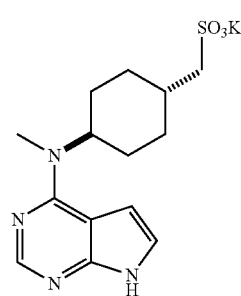

(E)

by reacting Intermediate C with a 7H-pyrrolo{2,3-d}pyrimidine analog, Intermediate D1,

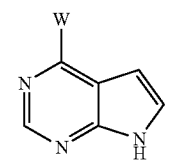

(D1)

wherein W is Cl, F, Br, I, O-triflate, O-mesyl, or O-tosyl; with a base in water or in an aqueous organic solvent containing about 1% to about 50% organic solvent at a temperature of about 60° C. to about 105° C. The preferred pyrimidine analog is Intermediate D, 4-chloro-7H-pyrrolo[2,3-d]pyrimidine (i.e., Intermediate D1 wherein W is Cl). The preferred amount of organic solvent is about 1% to about 20%. The more preferred amount of organic solvent is about 5%. The organic solvent includes alcohols (e.g., methanol, ethanol, propanol, and the like), ethers (e.g., tetrahydrofuran (THF), dioxane, dimethoxyethane, bis(2-methoxyethoxy)ethane, and the like), and polar aprotic solvents (e.g., N,N-dimethylformamide (DMF), acetone, acetonitrile, dimethylsulfoxide (DMSO), N-methylpyrrolidone (NMP), sulfolane, and the like). The preferred solvent for the reaction is a polar aprotic solvent. The more preferred organic solvent is NMP or sulfolane. The preferred aqueous organic solvent is about 5% NMP or sulfolane in water. The preferred aqueous organic solvent is about 5% NMP. The preferred reaction occurs in water. The base is selected from the group of bases consisting of carbonates (e.g., potassium, sodium, lithium, cesium, and the like), hydroxides (e.g., lithium, potassium, sodium, cesium, and the like) and organic bases such as trialkylamines, 1,8-diazabicycloundec-7-ene, and the like. The preferred base is a carbonate. The more preferred base is potassium carbonate. The preferred temperature for this reactive step is about 98° C. for about 12 hours. The reactants are cooled to about 30° C., and the resultant precipitated solids constitute Intermediate E which are isolated by filtration. The solids are washed with a mixture of water and alcohol (1:1), then an alcohol; or just washed with an alcohol; and dried under reduced pressure. The preferred alcohol is methanol.

In another aspect of the invention is a process for preparing Intermediate E by reacting Intermediate C with Intermediate D in water at about 98° C. for about 12 hours in the presence of potassium carbonate, cooling the reactants to about 30° C., isolating the solids by filtration, washing the solids with water:methanol (1:1) and then methanol or just washing with methanol, and drying the solids.

In another aspect of the invention is the process for converting Intermediate E, ((trans)-4-(methyl(7H-pyrrolo[2,3-d]pyrimidin-4-yl)amino)cyclohexyl)-methanesulfonic acid, potassium salt to the sulfonyl chloride, Intermediate F, ((trans)-4-(methyl(7H-pyrrolo[2,3-d]pyrimidin-4-yl)amino) cyclohexyl)-methanesulfonyl chloride,

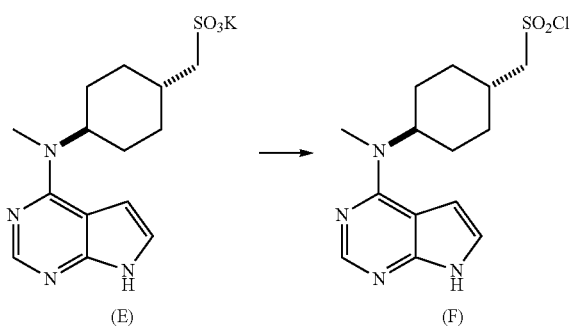

by reacting Intermediate E with a reagent known to effect this conversion. The reactant temperature ranges from about −20° C. to about 30° C. The preferred temperature ranges from about −10° C. to about 20° C. The more preferred temperature for this reaction is about 10° C. Common reagents known to effect this conversion include oxalyl chloride, thionyl chloride, phosphoryl chloride, phosphorus pentachloride, phosgene, triphosgene, and the like. The preferred reagent is oxalyl chloride, thionyl chloride, or phosphoryl chloride. The conversion from sulfonate salt to sulfonyl chloride can be conducted in an organic solvent that is compatible with the chloride reagent, for example, methylene chloride, acetonitrile (ACN), dichloroethane, dimethylformamide (DMF), dimethylacetamide (DMA), N-methylpyrrolidone (NMP), diisopropylformamide (DIPF), tetrahydrofuran (THF), 2-methyl-tetrahydrofuran, dimethoxymethane, dioxane, and the like, and mixtures thereof. A preferred solvent for this reaction is ACN or THF. A preferred solvent is ACN. Another preferred solvent is THF. Solvent mixtures can range from 85:15 to 99:1. Solvent mixtures include, for example, ACN:DMA (98:2), ACN:DIPF (97:3), THF:NMP (95:5), THF:DIPF (95:5), THF/DIPF (98:2), THF:DMA (90:10), ACN:DMF (85:15), and the like. In this instance, about 5% DIPF is added to the THF as a catalyst for the reaction. The sulfonate and organic solvent are combined and cooled to about 10° C. Oxalyl chloride, thionyl chloride, or phosphoryl chloride is added to the solvent mixture while stirring for about 1 hour to about 24 hours (preferably about 3 hours to about 10 hours, and more preferably about 1 hour to about 3 hours) while maintaining the temperature at about 10° C. to prepare Intermediate F. Intermediate F is not isolated, although it can be.

In another aspect of the invention is the process for converting the sulfonyl chloride (Intermediate F) to the sulfonamide Formula 1 compound. The sulfonyl chloride slurry (Intermediate F) that is already at about 10° C. is slowly added to a cold aqueous methylamine solution that is about −10° C. The methylamine solution is about 40% methylamine. After addition, about 10 to 15 volumes (1 volume=1 mL/gram), preferably 11 to 14 volumes, and more preferably about 14 volumes of water, is added to the mixture and the suspension is slowly heated to reflux. About 8 to 12 volumes, preferably about 10 volumes, of solvent are distilled off at about 65° C. to about 75° C. (i.e., about 100 mL for a 10 g scale reaction). The slurry is cooled to about 35° C., the solids are filtered, washed with water at room temperature, and dried. The resultant solids yield is about 92%. Alternatively, after addition of the cold methylamine, about 8 volumes of water can be added to the mixture and slowly refluxed, then distilling off about 5 volumes of solvent at about 65° C. to about 75° C., and then while distilling, add about 6 volumes of water and continue distillation until a total of about 10 volumes of solvent have been removed. Cool the slurry to about 35° C., filter, wash, and dry the solids as described above.

In another aspect of the invention is a process for preparing a compound of Formula 1, N-methyl-1-{trans-4-[methyl(7H-pyrrolo[2,3-d]pyrimidin-4-yl)amino]cyclohexyl}-methanesulfonamide,

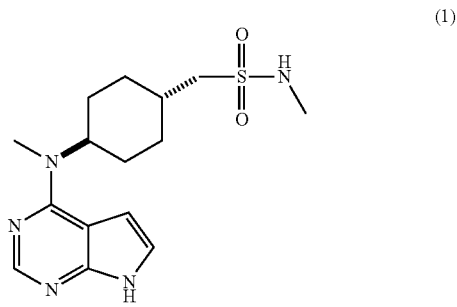

(1)

or a veterinary acceptable salt thereof, comprising
 a) reacting the compound, trans-4-((methylamino)cyclohexyl)methanesulfonic acid with a 7H-pyrrolo[2,3-d]pyrimidine analog in water or an aqueous organic solvent with a base at a reaction temperature of about 60° C. to about 105° C. to prepare the sulfonate salt;
 b) conversion of the sulfonate salt to the sulfonyl chloride intermediate in an organic solvent; and
 c) conversion of the sulfonyl chloride intermediate to the Formula 1 compound by reacting the sulfonyl chloride intermediate with a cold aqueous solution of methylamine.

In Step (a), the 7H-pyrrolo[2,3-d]pyrimidine analog is 4-chloro-7H-pyrrolo[2,3-d]pyrimidine and the reaction occurs in water or in an aqueous organic solvent that is 5% N-methylpyrrolidone or sulfolane, and the base is potassium carbonate and the reaction temperature is about 98° C. for about 12 hours. In Step (b), the conversion from the sulfonate salt to the sulfonyl chloride is prepared by reacting the sulfonate salt with oxalyl chloride, thionyl chloride, or phosphoryl chloride in an organic solvent which comprises acetonitrile or tetrahydrofuran, and wherein the reaction temperature is about 10° C. Further, the organic solvent further comprises N,N-dimethylacetamide, N,N-diisopropylformamide or N,N-dimethylformamide. The preferred solvent comprises tetrahydrofuran and N,N-diisopropylformamide. In Step (c), the cold aqueous methylamine is about 40% and is at about −10° C. In a preferred reaction, water is added to the reaction after addition of the sulfonyl chloride intermediate to the cold methylamine solution. The reactants are then slowly heated to reflux, and the solvents distilled off at a temperature of about 65° C. to about 75° C., the resultant solids are cooled to about 35° C., then the solids are filtered, washed with water at room temperature, filtered and dried. The resultant solids constitute the compound of Formula 1.

In yet another aspect of the invention is the process for preparing the Formula 1 compound, N-methyl-1-{trans-4-

[methyl(7H-pyrrolo[2,3-d]pyrimidin-4-yl)amino]cyclohexyl}-methanesulfonamide, comprising the steps of:
a) reacting the compound, trans-4-((methylamino)cyclohexyl)methanesulfonic acid (Intermediate C) with 4-chloro-7H-pyrrolo[2,3-d]pyrimidine (Intermediate D) and a base in water or an aqueous organic solvent comprising about 5% NMP or sulfolane at a temperature of about 60° C. to about 105° C., cooling the reactants to about 30° C., isolating the solids by filtration, washing the solids with water and methanol (1:1) and then methanol; or just washing the solids with methanol, and drying the sulfonate solids (Intermediate E);
b) conversion of the sulfonate (Intermediate E) to the sulfonyl chloride (Intermediate F) by adding the sulfonate solids to an organic solvent of acetonitrile or acetonitrile/DMA (98:2), or THF:DIPF (90:10 to 98:2), or THF:DMF (97:3 to 99:1); cooling the reactants to about 10° C., adding oxalyl chloride, thionyl chloride, or phosphoryl chloride while maintaining the reaction temperature at about 10° C. to prepare the sulfonyl chloride, Intermediate F;
c) conversion of Intermediate F to the Formula 1 compound by adding the reactants of Step (b) to a cold (about −10° C.) aqueous 40% methylamine solution;
d) adding water (about 14 volumes) and slowly heating the slurry to reflux, and distilling off about 10 volumes of solvent at about 65° C. to about 75° C. The reaction mixture is then slowly cooled back down to about 35° C.;
e) isolating the solids by filtration and washing the solids with water at room temperature, filtering and drying the solids.

In yet another aspect of the invention is the process for preparing the Formula 1 compound, N-methyl-1-{trans-4-[methyl(7H-pyrrolo[2,3-d]pyrimidin-4-yl)amino]cyclohexyl}-methanesulfonamide, comprising the steps of:
a) reacting the compound, trans-4-((methylamino)cyclohexyl)methanesulfonic acid (Intermediate C) with 4-chloro-7H-pyrrolo[2,3-d]pyrimidine (Intermediate D) and potassium carbonate in water at about 98° C. for about 12 hours, cooling the reactants to about 30° C., isolating the solids by filtration, washing the solids with water and methanol (1:1) and then methanol; or just washing the solids with methanol, and drying the sulfonate solids (Intermediate E);
b) conversion of the sulfonate (Intermediate E) to the sulfonyl chloride (Intermediate F) by adding the sulfonate solids to an organic solvent of THF:DIPF (95:5); cooling the reactants to about 10° C., adding oxalyl chloride or phosphoryl chloride while maintaining the reaction temperature at about 10° C. to prepare the sulfonyl chloride, Intermediate F;
c) conversion of the sulfonyl chloride solids, Intermediate F, to the Formula 1 compound by adding the reactants of Step (b) to a cold (about −10° C.) aqueous 40% methylamine solution;
d) adding about 14 volumes of water and slowly heating the slurry to reflux, distilling off about 10 volumes of solvent at about 65° C. to about 75° C. and then cooling the reactants to about 35° C.;
e) isolating the solids by filtration and washing the solids with water at room temperature, filtering and drying the solids.

In yet another aspect of the invention is the process for preparing the compound (trans-4-(methyl(7-tosyl-7H-pyrrolo[2,3-d]pyrimidin-4-yl)amino)-cyclohexyl)methane-sulfonic acid, potassium salt (Intermediate H)

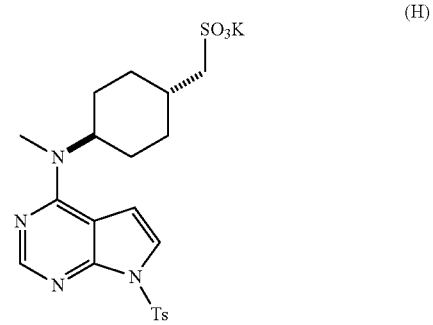

comprising the steps of:
a) reacting trans-4-((methylamino)cyclohexyl)methanesulfonic acid (Intermediate C) and 4-chloro-7-tosyl-7H-pyrrolo[2,3-d]pyrimidine (SigmaAldrich) in aqueous acetonitrile with a base at about 75° C.;
b) warming to about 80° C. and removing about 70% of the organic solvent by distillation;
c) adding n-butanol and discarding the lower aqueous layer;
d) heating the remaining organics and adding n-butanol; and
e) cooling to obtain the crystallized solids, Intermediate H.

In yet another aspect of the invention, is the process for preparing Intermediate H, comprising the steps of:
a) reacting trans-4-((methylamino)cyclohexyl)methanesulfonic acid (Intermediate C) and 4-chloro-7-tosyl-7H-pyrrolo[2,3-d]pyrimidine (SigmaAldrich) in aqueous acetonitrile which is about 40% with potassium carbonate at about 75° C. for about 4 hours;
b) warming to about 80° C. and removing about 70% of the organic solvent by distillation;
c) adding n-butanol and discarding the lower aqueous layer;
d) heating the remaining organics to about 65° C. and adding n-butanol; and
e) cooling the reactants to about 15° C. over about 3 hours to obtain the crystallized solids, Intermediate H.

In yet another aspect of the invention is the process for preparing the Formula 1 compound, N-methyl-1-{trans-4-[methyl(7H-pyrrolo[2,3-d]pyrimidin-4-yl)amino]cyclohexyl}-methanesulfonamide, comprising the steps of:
a) reacting (trans-4-(methyl(7-tosyl-7H-pyrrolo[2,3-d]pyrimidin-4-yl)amino)-cyclohexyl)methanesulfonic acid, potassium salt (Intermediate H) with thionyl chloride in an organic solvent comprising THF and DMF and heating to about 35° C. for about 4 hours;
b) cooling the reactants to about 0° C. and slowly adding water while maintaining the temperature below about 15° C.;
c) adding the reactants to an aqueous solution of 20% methylamine while maintaining the temperature below about 15° C.;
d) warming the reactants to about 35° C., allowing phase separation, and discarding the lower aqueous layer;
e) adding aqueous KOH and heating to reflux for about 4 hours;
f) adding water and distilling the solution until the internal temperature is about 70° C.;

g) cooling the slurry to about 10° C.; and h) isolating the solids (Formula 1 compound) by filtration.

In another aspect of the invention, is a process for preparing the maleate salt of the Formula 1 compound, comprising the steps of:

a) reacting N-methyl-1-{trans-4-[methyl(7H-pyrrolo[2,3-d]pyrimidin-4-yl)amino]cyclohexyl}-methanesulfonamide with maleic acid in water;

b) heating the reactants to about 60° C.;

c) cooling the solution to about 55° C. and seeding with a previously prepared maleic acid salt of the Formula 1 compound;

d) cooling to about 37° C. at a rate of about 1° C. per hour and then to about 5° C. at a rate of about 3° C. per hour; and e) isolating the solids by filtration.

In another aspect of the invention is a compound selected from (4-(methylamino)phenyl)methanesulfonic acid; trans-4-((methylamino)cyclohexyl)methanesulfonic acid; trans-4-(methyl(7H-pyrrolo[2,3-d]pyrimidin-4-yl)amino)cyclohexyl)methane sulfonic acid, potassium salt; trans-4-(methyl(7H-pyrrolo[2,3-d]pyrimidin-4-yl)amino) cyclohexyl)methane sulfonic acid, sodium salt; ((trans)-4-(methyl(7H-pyrrolo[2,3-d]pyrimidin-4-yl)amino) cyclohexyl)-methanesulfonyl chloride; (trans-4-(methyl(7-tosyl-7H-pyrrolo[2,3-d]pyrimidin-4-yl)amino)-cyclohexyl) methane-sulfonic acid, potassium salt; and (trans-4-(methyl (7-tosyl-7H-pyrrolo[2,3-d]pyrimidin-4-yl)amino)-cyclohexyl)methane-sulfonic acid, sodium salt.

In yet another aspect is the compound (4-(methylamino) phenyl)methanesulfonic acid. In yet another aspect is the compound trans-4-((methylamino)cyclohexyl)-methanesulfonic acid. In yet another aspect is the compound trans-4-(methyl(7H-pyrrolo[2,3-d]pyrimidin-4-yl)amino)cyclohexyl)methane sulfonic acid, potassium salt. In yet another aspect is the compound trans-4-(methyl(7H-pyrrolo[2,3-d] pyrimidin-4-yl)amino)cyclohexyl)methane sulfonic acid, sodium salt. In yet another aspect is the compound ((trans)-4-(methyl(7H-pyrrolo[2,3-d]pyrimidin-4-yl)amino)cyclohexyl)-methanesulfonyl chloride. In yet another aspect is the compound (trans-4-(methyl(7-tosyl-7H-pyrrolo[2,3-d]pyrimidin-4-yl)amino)-cyclohexyl)methane-sulfonic acid, potassium salt. In yet another aspect is the compound (trans-4-(methyl(7-tosyl-7H-pyrrolo[2,3-d]pyrimidin-4-yl)amino)-cyclohexyl)methane-sulfonic acid, sodium salt.

In another aspect of the invention are veterinary compositions which comprise a veterinary acceptable carrier and a compound of Formula 1 prepared from the processes described herein.

In yet another aspect of the invention is a method of using or the use of the compound of Formula 1 prepared from the processes as described herein for controlling or treating a disorder or condition selected from allergic reactions, allergic dermatitis, atopic dermatitis, eczema, pruritis, asthma and other obstructive airway diseases selected from chronic asthma, inveterate asthma, late asthma, airway hyper-responsiveness bronchitis, bronchial asthma, allergic asthma, intrinsic asthma, extrinsic asthma, dust asthma, recurrent airway obstruction, and chronic obstruction pulmonary disease, autoimmune diseases selected from rheumatoid arthritis, autoimmune thrombocytopenia, autoimmune hemolytic anemia, systemic lupus erythematosus, bullous pemphigoid, and alopecia, cancer selected from mammary cancer, bone cancer, prostate cancer, bladder cancer, melanoma, mast cell carcinoma, squamous cell carcinoma, lymphoma, and leukemia, inflammatory bowel disease, eosinophilic gastroenteritis, mastocytosis, keratoconjunctivitis, and keratoconjunctivitis sicca in a mammal.

In yet another aspect of the invention is a method of using or the use of the compound of Formula 1 prepared from the processes as described herein for controlling or treating a disorder or condition selected from allergic reactions, allergic dermatitis, atopic dermatitis, pruritis, asthma and other obstructive airway diseases selected from chronic asthma, inveterate asthma, late asthma, airway hyper-responsiveness bronchitis, bronchial asthma, allergic asthma, intrinsic asthma, extrinsic asthma, dust asthma, recurrent airway obstruction, and chronic obstruction pulmonary disease in a mammal. Preferred methods of use or uses thereof include controlling or treating a disorder or condition selected from allergic reactions, allergic dermatitis, atopic dermatitis, and pruritis.

In yet another aspect of the invention is the use of the compound of Formula 1 prepared from the processes as described herein to prepare a medicament for administration to a mammal in need thereof.

DETAILED DESCRIPTION

Figure 1:
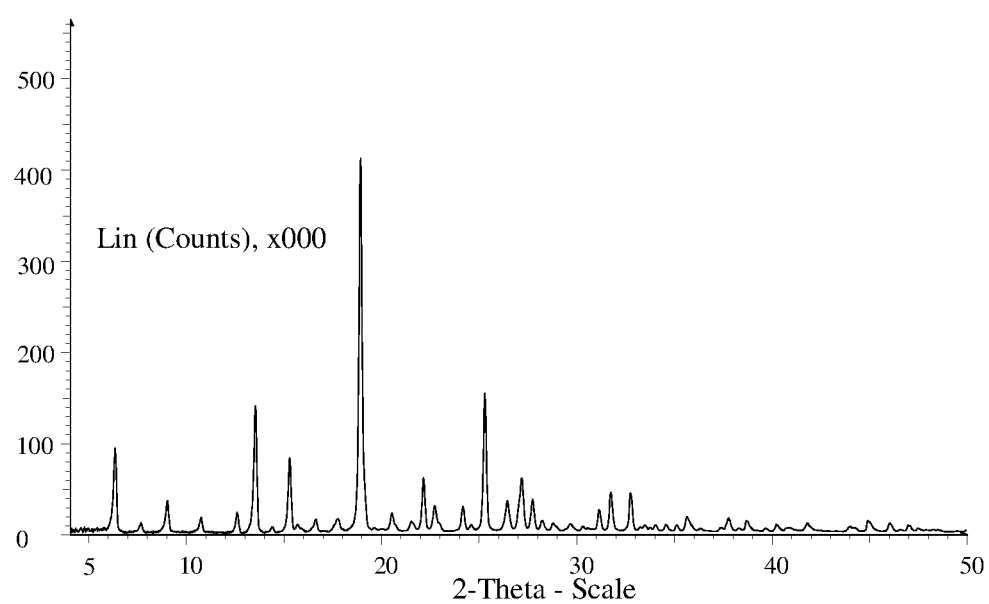
FIG. 1. Depicts an illustrative PXRD pattern of crystalline Form B(A).

With respect to the Formula 1 compound, N-methyl-1-{trans-4-[methyl(7H-pyrrolo[2,3-d]pyrimidin-4-yl)amino] cyclohexyl}-methanesulfonamide, intermediates thereof, and veterinary acceptable salts thereof, the following terms have the meanings defined below.

Definitions

"About", as used herein, refers to the indicated value of the variable and to all values of the variable that are within the experimental error of the indicated value (e.g., within the 95% confidence interval for the mean) or within 10 percent of the indicated value, whichever is greater.

"Controlling", "treating" or "treatment" of a disease includes: (1) preventing the disease, i.e. causing the clinical symptoms or signs of the disease not to develop in a mammal that may be exposed to or predisposed to the disease but does not yet experience or display symptoms/ signs of the disease; (2) inhibiting the disease, i.e., arresting or reducing the development of the disease or its clinical symptoms/signs; or (3) relieving the disease, i.e., causing regression of the disease or its clinical symptoms/signs.

"Mammal", as used herein, refers to human and non-human animals. Animal(s) includes both livestock and companion animals. The phrase "companion animal" or "companion animals" refers to animals kept as pets. Examples of companion animals include cats, dogs, and horses. The term "livestock" refers to animals reared or raised in an agricultural setting to make products such as food or fiber, or for its labor. In some embodiments, livestock are suitable for consumption by humans. Examples of livestock animals include cattle, goats, horses, pigs, sheep, including lambs, and rabbits, as well as birds, such as chickens, ducks and turkeys.

"Percent" (%), as used herein, refers to individual percent values. When referring to % in liquids (volume/volume % or v/v %) like an aqueous organic solvent, the % is the volume % of the solvent in the total volume of the solution (e.g., 5% NMP=5 mL NMP and 95 mL water). When referring to % for solids in liquids (weight/volume % or w/v %), the % value is construed to be the weight of the solid in the total volume of the solution and refers to the number of grams of solute in 100 mL of solution. When referring to solids (weight % or w/w %) refers to the weight (mass) of one component relative to the total weight (mass) of the solid composition.

"Therapeutically effective amount", as used herein, refers to the amount of a compound that, when administered to a mammal for treating a disease, is sufficient to effect such treatment for the disease. The "therapeutically effective amount" will vary depending on the compound, the disease and its severity and the age, weight, etc., of the mammal to be treated. In the instant case, the therapeutically effective amount is about 0.4 mg/kg to about 0.6 mg/kg.

"Veterinary acceptable" means suitable for use in non-human animals.

Compounds that have the same molecular formula but differ in the nature or sequence of bonding of their atoms or the arrangement of their atoms in space are termed "isomers". Isomers that differ in the arrangement of their atoms in space are termed "stereoisomers". It will be appreciated by those skilled in the art that the compound of Formula 1 can exist as cis- and trans-achiral diastereomers. Specifically, the present invention provides processes for preparing a compound of Formula 1, which has the chemical name N-methyl-1-{trans-4-[methyl(7H-pyrrolo[2,3-d]pyrimidin-4-yl)amino]cyclohexyl}-methanesulfonamide,

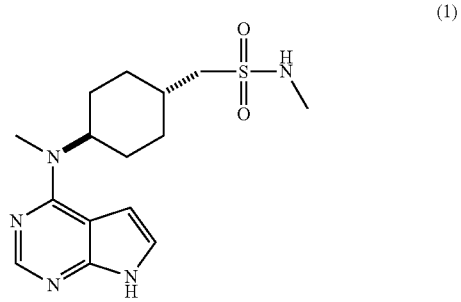

(1)

or a veterinary acceptable salt thereof.

Included within the scope of the present invention are all isomers (e.g. cis-, trans-achiral diastereomers) of the Intermediates described herein alone as well as any mixtures thereof, including those of Formula 1.

Stereoisomeric mixtures, e.g. mixtures of diastereomers, can be separated into their corresponding isomers in a known manner by means of suitable separation methods. Diastereomeric mixtures for example may be separated into their individual diastereomers by means of fractionated crystallization, chromatography, solvent distribution, and similar procedures. This separation may take place either at the level of one of the starting compounds or in a compound of Formula 1 itself.

Routes of Administration

In therapeutic use for treating disorders in an animal, the compound (Formula 1) of the present invention or its veterinary compositions can be administered orally, parenterally, topically, rectally, transmucosally, or intestinally. Parenteral administrations include indirect injections to generate a systemic effect or direct injections to the afflicted area. Topical administrations include the treatment of skin or organs readily accessible by local application, for example, eyes or ears. It also includes transdermal delivery to generate a systemic effect. The rectal administration includes the form of suppositories. The preferred routes of administration are oral and parenteral.

Veterinary Salts

The compound of Formula 1 may be used in its native form or as a salt. In cases where forming a stable nontoxic acid or base salt is desired, administration of the compound as a veterinary acceptable salt may be appropriate. Veterinary acceptable salts of the Formula 1 compound include the acetate, ascorbate, aspartate, benzoate, besylate, bicarbonate/carbonate, bisulphate/sulphate, borate, camsylate, citrate, edisylate, etoglutarate, esylate, formate, fumarate, gluceptate, gluconate, glucuronate, glycerophosphate, hexafluorophosphate, hibenzate, hydrochloride/chloride, hydrobromide/bromide, hydroiodide/iodide, isothionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. A preferred salt is the maleate salt.

Composition/Formulation

Veterinary compositions of the present invention may be manufactured by processes well known in the art, e.g., by means of conventional mixing, dissolving, granulation, dragee-making, levigating, emulsifying, encapsulating, entrapping, lyophilizing processes or spray drying. Veterinary compositions for use in accordance with the present invention may be formulated in conventional manner using one or more veterinary acceptable carriers comprising excipients and auxiliaries, which facilitate processing of the active compound into preparations, which can be used as a pharmaceutical. Proper formulation is dependent upon the route of administration chosen. Veterinary acceptable excipients and carriers are generally known to those skilled in the art and are thus included in the instant invention. Such excipients and carriers are described, for example, in "Remingtons Pharmaceutical Sciences" Mack Pub. Co., New Jersey (1991). The formulations of the invention can be designed to be short-acting, fast-releasing, long-acting, and sustained-releasing. Thus, the veterinary formulations can also be formulated for controlled release or for slow release.

Dosage

Veterinary compositions suitable for use in the present invention include compositions wherein the active ingredients are contained in an amount sufficient to achieve the intended purpose, i.e., control or the treatment of disorders or diseases. More specifically, a therapeutically effective amount means an amount of compound effective to prevent, alleviate or ameliorate symptoms/signs of disease or prolong the survival of the subject being treated. The quantity of active component, which is the Formula 1 compound of this invention, in the veterinary composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.01 mg/kg to about 100 mg/kg of body weight/day, preferably about 0.1 mg/kg to about 10 mg/kg of body weight/day, more preferably about 0.3 mg/kg to about 3 mg/kg of body weight/day, even more preferably about 0.3 mg/kg to about 1.5 mg/kg of body weight/day, and even more preferably about 0.4 mg/kg to about 0.6 mg/kg of body weight per day. A preferred dosage regimen is to orally administer about 0.4 mg/kg to about 0.6 mg/kg of body weight per day for up to 14 days and then orally administered at a dose of about 0.4 mg/kg to about 0.6 mg/kg of body weight once daily for maintenance therapy. Tablet strengths of the maleate salt of the Formula 1 compound are provided in doses of 3.6 mg, 5.4 mg, and 16 mg. These tablets can be administered in varying proportions so as to ensure a dose of about 0.4 to 0.6 mg/kg of body weight for once a day or twice daily dosing. It is to be understood that the dosages may vary depending upon the requirements of each subject and the severity of the disorders or diseases being treated. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

Medical and Veterinary Uses

The compound of the present invention is a Janus Kinase inhibitor (JAK-i) with efficacy against Janus Kinase-1 (JAK-1), Janus Kinase-2 (JAK-2) and Janus Kinase-3 (JAK-3), and particularly, JAK-1. Accordingly, it is useful as a therapeutic agent for cancer, asthma, atopic dermatitis, autoimmune disorders, control of pruritus, chronic respiratory disease and other indications where immunosuppression/immunomodulation would be desirable. A preferred use is for the control of pruritus associated with allergic dermatitis and control of atopic dermatitis in canines.

The Formula 1 compound may be administered in a veterinary acceptable form either alone or in combination with one or more additional agents which modulate a mammalian immune system or with anti-inflammatory agents. These agents may include but are not limited to cyclosporin A, rapamycin, FK-506 (tacrolimus), leflunomide, deoxyspergualin, mycophenolate, azathioprine, daclizumab, aspirin, acetaminophen, ibuprofen, naproxen, piroxicam, and antiinflammatory steroids (e.g. prednisolone or dexamethasone). These agents may be administered as part of the same or separate dosage forms, via the same or different routes of administration, and on the same or different administration schedules according to standard veterinary practice known to one skilled in the art.

The JAK kinases, including JAK-3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood 89:4146-52; Kaneko et al., (1997), Clin. Exp. Immun. 109:185-193; and Nakamura et al., (1996), J. Biol. Chem. 271: 19483-8). They are also known to be important to lymphocyte differentiation, function and survival. JAK-3 in particular plays an essential role in the function of lymphocytes, macrophages, and mast cells. Given the importance of this JAK kinase, compounds which modulate the JAK pathway, including those selective for JAK-3, can be useful for treating diseases or conditions where the function of lymphocytes, macrophages, or mast cells is involved (Kudlacz et al., (2004) Am. J. Transplant 4:51-57; Changelian (2003) Science 302:875-878).

Conditions in which targeting of the JAK pathway or modulation of the JAK kinases are contemplated to be therapeutically useful include, arthritis, asthma, autoimmune diseases, cancers or tumors, diabetes, certain eye diseases, disorders or conditions, inflammation, intestinal inflammations, allergies, neurodegenerative diseases, psoriasis, transplant rejection, and viral infection. Conditions which can benefit for inhibition of JAK are discussed in greater detail below.

Accordingly, the compound of Formula 1 or its veterinary acceptable salts and veterinary compositions can be used to treat a variety of conditions or diseases such as:

asthma and other obstructive airways diseases, including chronic or inveterate asthma, late asthma, airway hyperresponsiveness, bronchitis, bronchial asthma, allergic asthma, intrinsic asthma, extrinsic asthma, dust asthma, recurrent airway obstruction, and chronic obstruction pulmonary disease;

autoimmune diseases or disorders, including those designated as single organ or single cell-type autoimmune disorders, for example autoimmune hemolytic anemia, autoimmune atrophic gastritis of pernicious anemia, autoimmune encephalomyelitis, autoimmune orchitis, autoimmune thrombocytopenia, sympathetic ophthalmia, ulcerative colitis and membranous glomerulopathy, those designated as involving systemic autoimmune disorder, for example systemic lupus erythematosis, systemic sclerosis, and bullous pemphigoid, and additional autoimmune diseases, which can be O-cell (humoral) based or T-cell based, including autoimmune alopecia and thyroiditis;

cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors; Eye diseases, disorders or conditions including autoimmune diseases of the eye, keratoconjunctivitis and keratoconjunctivitis sicca (dry eye);

intestinal inflammations, allergies or conditions including ulcerative colitis, inflammatory bowel disease, coeliac diseases, proctitis, eosinophilic gastroenteritis, and mastocytosis;

skin diseases, conditions or disorders including atopic dermatitis, eczema, psoriasis, scleroderma, pruritus and other pruritic conditions;

allergic reactions including allergic dermatitis in mammal including horse allergic diseases such as bite hypersensitivity, summer eczema and sweet itch in horses.

Another embodiment provides a method of inhibiting a JAK enzyme, including JAK-1, JAK-2, JAK-3 and/or Tyk-2 that includes contacting the JAK enzyme with either a non-therapeutic amount or a therapeutically effective amount of the Formula 1 compound. Such methods can occur in vivo or in vitro. In vitro contact can involve a screening assay to determine the efficacy of the Formula 1 compound against a selected enzyme at various amounts or concentrations. In vivo contact with a therapeutically effective amount of the Formula 1 compound can involve treatment of a described disease, disorder or condition or prophylaxis of organ transplant rejection in the animal in which the contact occurs. The effect of the Formula 1 compound on the JAK enzyme and/or host animal can also be determined or measured. Methods for determining JAK activity include those described in WO1999/65908 and WO2007/012953.

The following reaction schemes illustrate the general synthetic procedures for preparing the compound of Formula 1. All starting materials are prepared by procedures described in these schemes or by procedures known to one of ordinary skill in the art.

The following non-limiting reagents were used to prepare the intermediates and the Formula 1 compound described herein: tetrahydrofuran (THF); N,N-dimethylformamide (DMF); N,N-dimethylacetamide (DMA); N-methylpyrrolidone (NMP); 1,8-diazabicycloundec-7-ene (DBU), dimethylsulfoxide (DMSO), N,N-diisopropylformamide (DIPF), methanol (MeOH), ethanol (EtOH), potassium hydroxide (KOH), and acetonitrile (ACN). The 40% aqueous solution of methylamine can be purchased commercially (e.g., SigmaAldrich). Intermediate G (4-chloro-7-tosyl-7H-pyrrolo[2,3-d]pyrimidine) can also be purchased from SigmaAldrich.

Scheme 1: Preparation of Intermediate C, trans-4-((methylamino)cyclohexyl)-methanesulfonic acid.

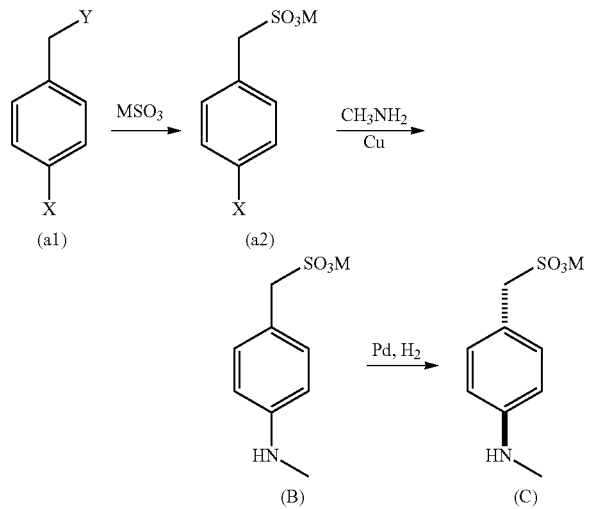

Starting with Intermediate a1, Y is displaced with a sulfite salt (e.g., M is potassium, sodium, or calcium) in water containing 0 to about 50% of an organic solvent such as acetonitrile, acetone, water miscible alcohols (e.g., methanol, ethanol, propanol, and the like), or water-miscible ethers (e.g., THF, diethyl ether, dioxane, and the like) to prepare Intermediate a2. Y can be any functional group that is susceptible to nucleophilic displacement by sulfite, for example Y can be Cl, Br, I, O-tosyl, O-mesyl, O-triflates, and the like. X is Br but can also be I. The preferred starting material is 4-bromobenzyl bromide (i.e., Intermediate a1 wherein X and Y are both Br) which is commercially available. The reaction can be run between about 50° C. and reflux. Starting with 4-bromobenzylbromide and reacting with sodium sulfite under the reaction conditions described herein, provides sodium (4-bromophenyl)methanesulfonate, Intermediate A.

Secondly, Intermediate B is prepared by nucleophilic displacement of bromine from Intermediate A in water containing about 5% to about 40% methylamine. The copper catalyst can be copper(0) or any copper(1) salt and the loading of catalyst can be any amount greater than about 0.25 mol %. The preferred catalyst is the copper(1) salt, CuBr at about 2 mol %. The reaction can be run at temperatures greater than about 50° C. Subsequently, the sulfite salt is protonated with addition of an acid to prepare Intermediate B. In the third step, Intermediate B undergoes catalytic hydrogenation under mild conditions using palladium to prepare the trans-specific Intermediate C. Known scientific literature (e.g., US Patent Application publication 2009-0143302, U.S. Pat. No. 4,424,213, and Nair, M. G., J. Med Chem. 1983, 26(2), pg. 135) describes hydrogenation of 4-substituted N-alkyl anilines with more reactive metal catalysts (e.g., Rh, Pt and PtO$_2$) that predominantly produce cis-specific geometric analogs. Preferably, hydrogenation occurs with hydrogen gas under pressure (about 20 psi to about 70 psi) using Pd(0) on carbon in a solvent of water and methanol. The final reaction prepares the trans-geometry of Intermediate C at a ratio of about 70:30 (trans:cis). The trans-specific product can be purified to >99% by crystallization from an aqueous alcohol (e.g., methanol, ethanol, isopropanol, and the like). Alternatively, Intermediate C can be prepared from Intermediate B using Pd(0) or an un-reduced palladium (Pd(II)) catalyst such as Pd(OH)$_2$ under hydrogen transfer conditions using formic acid or formic acid salts as the hydrogen source.

Scheme 2: Preparation of Formula (1) Compound

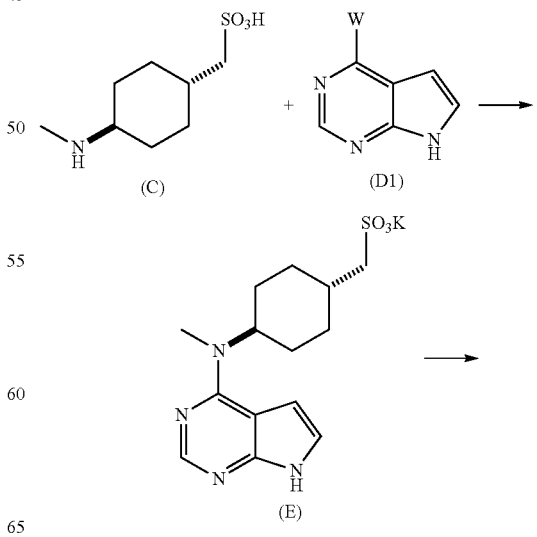

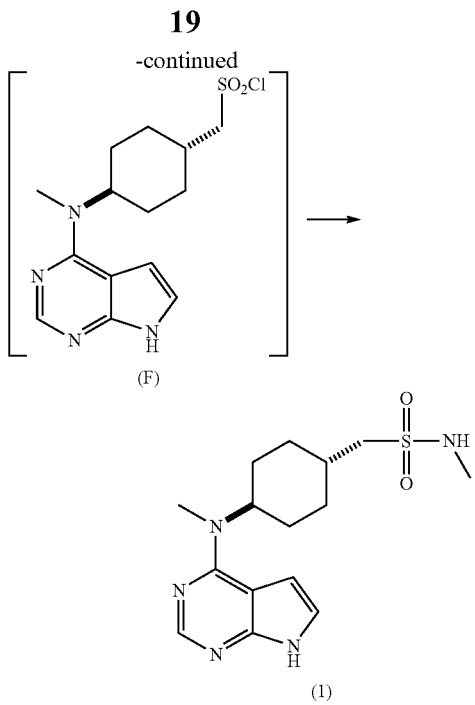

In the first step, Intermediate C is reacted with a 7H-pyrrolo[2,3-d]pyrimidine analog (Intermediate D1) to prepare a sulfonate salt. The preferred D1 intermediate is 4-chloro-7H-pyrollo[2,3-d]pyrimidine (Intermediate D; i.e., W of D1 is Cl) which is a readily available commercial compound that is used in the coupling reaction to prepare the sulfonate salt (Intermediate E). The functionality W in Intermediate D analog need not be Cl, but can be any easily displaceable functional group (such as F, Br, I, O-triflate, O-mesyl, O-tosyl, and the like). The preferred solvent is water with about 5% NMP or sulfolane, but the reaction can be run in water alone or with the addition of about O-50% of another water-miscible organic solvent, including water-miscible alcohols (e.g., methanol, ethanol, propanol, and the like), water miscible ethers (THF, dimethyl ether, bis(2-methoxyethyl)ether, dioxane, and the like), and polar aprotic solvents (e.g., acetone, acetonitrile, DMSO, DMF, and the like). This alternative process also requires a base which is preferentially potassium carbonate, but can also be other carbonates (e.g., lithium, sodium, or cesium), hydroxides (lithium, potassium, sodium, or cesium), or organic bases such as trialkylamines (e.g., triethylamine, diisopropylethylamine, and the like), and 1,8-diazbicycloundec-7-ene (DBU). The reaction temperature for this reaction is at least about 60° C. to about 105° C. The preferred temperature is about 98° C.

The second step is the conversion of the sulfonate salt (Intermediate E) to the methylsulfonamide of Formula 1 via conversion through the sulfonyl chloride (Intermediate F) using oxalyl chloride, phosphoryl chloride, thionyl chloride, or any other reagent known to effect this conversion (e.g., phosphorus pentachloride, phosgene, triphosgene, and the like). The preferred solvent for this reaction is acetonitrile or THF, but other solvents which are compatible with oxalyl chloride or phosphoryl chloride, and the other chloride reagents have been shown to work such as methylene chloride, dichloroethane, DMF, DMA, NMP, DIPF, THF, 2-methyl tetrahydrofuran, dimethoxyethane, dioxane and the like. Mixtures of these solvents is also contemplated, for example, THF and DMA, THF and DIPF. This reaction is preferentially run at temperatures between about 0° C. and about 20° C. but is not limited to that range. The preferred reaction temperature is about 10° C. The sulfonyl chloride (Intermediate F) is reacted with cold methylamine to form the methyl sulfonamide of Formula 1. Preferably, the methylamine is cold (about −15° C. to about 0° C.) and is 40% aqueous methylamine; but gaseous methylamine and methylamine dissolved in organic solvents (such as THF or ethanol) can work.

Alternate Synthesis to Prepare the Formula 1 Compound with a Tosyl Intermediate

This alternate conversion is shown below in Scheme 3. Intermediate C is reacted with Intermediate G (a commercially available compound, 4-chloro-7-tosyl-7H-pyrrolo[2,3-d]pyrimidine; i.e., Ts is tosyl)) to produce the coupled Intermediate H (CAS 1208319-30-5). The reaction is preferably run in a 40/60 mixture of acetonitrile/water, but other organic solvents such as 2-propanol, THF, and dioxane can be used. A base is required for the reaction and is preferably at least 1.5 equivalents of potassium carbonate, but other organic bases (e.g., carbonates, trialkylamines, DBU, and the like) can be used. The reaction is preferably run at about 75° C. or higher, but can be run as low as about 50° C. Intermediate H is isolated by crystallization from a mixture of n-butanol/water or from water alone.

Scheme 3: Preparation of the Tosyl Intermediate H

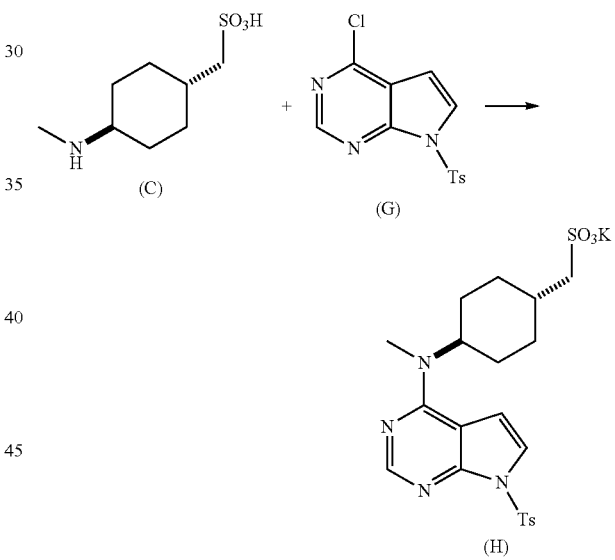

The following procedural steps and examples illustrate the processes for preparing the intermediates of Formula 1 and the Formula 1 compound of the present invention.

EXAMPLES

Intermediate A: Sodium (4-bromophenyl)methanesulfonate

To a flask containing 4-bromobenzylbromide (500 g, 2.00 mol) and sodium sulfite (296 g, 1.15 eq) was charged water (1.25 L) and acetonitrile (220 mL). The slurry was heated at about 80° C. with stirring for about 4 hours and was then cooled to about 10° C. The solids were isolated by filtration and were dried under vacuum to afford 547 g of a white solid (Intermediate A). $^1$H NMR (D$_2$O, 600 MHz): 7.44 (d, 2H), 7.18 (d, 2H), 4.00 (s, 2H). MS: M+H−Na=251.

Intermediate B: (4-(methylamino)phenyl)methanesulfonic Acid

To a flask containing sodium (4-bromophenyl)methanesulfonate (Intermediate A, 1.00 kg, 366 mmol) was added copper(I) bromide (10.3 g), water (1.2 L) and 40% aqueous methylamine (0.85 L). The flask was sealed and the reaction was heated at about 90° C. for about 16 hours. The reaction was cooled to about 65° C. and a solution of citric acid (68 g) in water (130 mL) was added and stirred for about 20 minutes to remove copper residuals. To the reaction was added water (1.4 L) and the pH was adjusted to 3.2 with concentrated aqueous hydrochloric acid. The white slurry was cooled to about 15° C. and then the product was isolated by filtration. The product was washed with water (0.7 L) and then dried under vacuum to produce 630 g of a white solid (Intermediate B). $^1$H NMR (D$_2$O, 600 MHz): 7.42 (d, 2H), 7.31 (d, 2H), 4.07 (s, 2H), 2.93 (s, 3H). MS: M+H=202.

Intermediate C: trans-4-((methylamino)cyclohexyl)methanesulfonic Acid

To a hydrogenation vessel containing (4-(methylamino) phenyl)methanesulfonic acid (100 gm, 498 mmol, Intermediate B) was added water (375 mL), methanol (125 mL) and 10% palladium on carbon (50% wet, 6 g). The reaction was heated to about 70° C. and hydrogen (30 psi) pressure was maintained for about 16 hours. The catalyst was removed by filtration. The reaction was concentrated under reduced pressure to a volume of 180 mL. To this solution was added 800 mL ethanol. The reaction was heated to about 45° C. and then cooled over about 4 hours to about 0° C. The product was isolated by filtration, was washed with ethanol (100 mL), and was dried under vacuum to produce 45 g of a white solid (Intermediate C). $^1$H NMR (D$_2$O, 600 MHz): 2.91 (s, m), 2.71 (d, 2H), 2.54 (s, 3H), 1.99 (dd, 4H), 1.70 (m, 1H), 1.28 (dq, 2H), 1.05 (dq, 2H); M+H=208

Intermediate E: ((trans)-4-(methyl(7H-pyrrolo[2,3-d]pyrimidin-4-yl)amino)cyclohexyl)-methanesulfonic Acid, Potassium Salt To a flask containing trans-4-((methylamino)cyclohexyl) methanesulfonic acid (5.0 g, 24 mmol, Intermediate C), 4-chloro-7H-pyrrolo[2,3-d]pyrimidine (3.5 g, 22.8 mmol, Intermediate D (Intermediate D1 wherein W is Cl) and potassium carbonate (5.77 g, 41 mmol) was added water (27 mL). The mixture was heated at about 98° C. for about 12 hours, was cooled to about 30° C. and was filtered. The solids were washed with methanol (32 mL). After drying at about 60° C. under reduced pressure, this afforded 7.46 g of a white powder (Intermediate E). $^1$H NMR (DMSO-d6, 600 MHz): 11.7 (s, 1H), 8.07 (s, 1H), 7.11 (d, 1H), 6.51 (s, 1H), 4.55 (brs, 1H), 3.14 (s, 3H), 2.37 (d, 2H), 2.10 (br d, 2H), 1.71 (m, 1H), 1.64 (m, 4H), 1.09 (m, 2H). M+H-K=324

Preparation of Formula 1: N-methyl-1-{trans-4-[methyl(7H-pyrrolo[2,3-d]pyrimidin-4-yl)amino]cyclohexyl}methanesulfonamide A slurry of ((trans)-4-(methyl(7H-pyrrolo[2,3-d]pyrimidin-4-yl)amino)cyclohexyl)methanesulfonic acid, potassium salt (Intermediate E) (10.0 g, 27.6 mmol) in acetonitrile (30 mL) or THF (100 mL) with DMF (0.5 mL) or DIPF (5 mL) was cooled to about 10° C. To this was added oxalyl chloride (45 mmol, 3.9 mL, 5.7 g (1.65 eq)) or phosphoryl chloride (49.68 mmol, 4.6 mL, 1.8 eq) slowly and the slurry kept at about 10° C. and stirred for at least about 1 hour to about 3 hours to prepare the ((trans)-4-(methyl(7H-pyrrolo [2,3-d]pyrimidin-4-yl)amino)cyclohexyl)-methanesulfonyl chloride intermediate (Intermediate F). The reactants were slowly added to a cold (about −10° C.) solution of aqueous methylamine (40%, 30 mL, 330 mmol). After the addition was complete, water (114 mL) was added and the reaction was slowly warmed to about 65° C. to about 75° C. for about 2 hours, during which time about 100 ml of solvent was distilled, then slowly cooled to about 35° C. for about 1 hour, and the solids were isolated by filtration. The solids were further washed with 40 mL of water at room temperature, and the product was isolated by filtration. The solids were dried under vacuum to afford 8.3 g of a white solid (Formula 1 compound). $^1$H NMR (DMSO-d6, 600 MHz): 11.6 (s, 1H), 8.09 (s, 1H), 7.13 (t, 1H), 6.54 (s, 1H), 4.68 (br s, 1H), 3.17 (s, 3H), 2.96 (d, 3H), 2.59 (d, 2H), 2.05 (br d, 2H), 1.85 (m, 1H), 1.69 (m, 4H), 1.29 (m, 2H). M+H=338.

Alternatively, the Formula 1 compound can be prepared using the tosyl protected sodium sulfonate.

Intermediate H: (trans-4-(methyl(7-tosyl-7H-pyrrolo[2,3-d]pyrimidin-4-yl)amino)-cyclohexyl)methanesulfonic Acid, Potassium Salt To a flask containing trans-4-((methylamino)cyclohexyl) methanesulfonic acid (Intermediate C, 44.0 g, 212 mmol) and 4-chloro-7-tosyl-7H-pyrrolo[2,3-d]pyrimidine (60.0 g, 195 mmol, Intermediate G) was added water (120 mL), acetonitrile (90 mL) and potassium carbonate (70.8 g, 507 mmol). The solution was heated at about 75° C. for about 4 hours and was then warmed to about 80° C. and about 65 mL of solvent was removed by distillation. To the reaction was charged n-butanol (300 mL) and water (40 mL). The reaction was warmed to about 70° C. and the lower aqueous layer was removed and discarded. The remaining organics were heated to about 70° C. and an additional amount of n-butanol (600 mL) was added. The solution was cooled to about 15° C. over about 3 hours. The product crystallized during this time and was isolated by filtration and was washed with n-butanol (100 mL). The product was dried at about 60° C. under vacuum to afford 94.7 g of a white powder (Intermediate H). $^1$H NMR (DMSO-d6, 600 MHz): 8.22 (s, 1H), 7.97 (d, 2H), 7.59 (d, 1H), 7.44 (d, 2H), 6.80 (br s, 1H), 4.7 (br s, 1H), 3.12 (s, 3H), 2.37 (s, 3H), 2.35 (d, 2H), 2.07 (m, 2H), 1.74 (m, 1H), (1.60 (m, 4H), 1.08 (m, 2H). MS M+H-Na=479

Preparation of the Formula 1 Compound from Intermediate H

To a flask was charged the tosyl potassium sulfate (Intermediate H) (70 g, 135 mmol), THF (490 mL), DMF (1 g, 13 mmol) and thionyl chloride (29.1 g, 244 mmol). The reaction was heated to about 35° C. for about 3 hours and was then cooled to about 0° C. Water (2 mL) was added slowly while maintaining the temperature below about 15° C. A solution of aqueous methylamine (20% in water, 188 mL) was cooled to about −5° C. The reactants were added to the cooled methylamine solution at a rate such that the temperature did not exceed about 10° C. The reaction was warmed to about 35° C. and the lower aqueous layer was discarded. A 45% aqueous potassium hydroxide (38 g, 305 mmol) solution was added to the remaining organic phase. The reaction was heated at reflux for about 4 hours. To the reaction was charged additional water (450 mL) and the solution was distilled until the internal temperature reached about 75° C. The resulting slurry was cooled to about 10° C. and the product was isolated by filtration. The product was dried under vacuum to afford 39 g of a white solid (Formula 1). 1H NMR (DMSO-d6, 600 MHz): 11.6 (s, 1H), 8.09 (s, 1H), 7.13 (t, 1H), 6.54 (s, 1H), 4.68 (br s, 1H), 3.17 (s, 3H), 2.96 (d, 3H), 2.59 (d, 2H), 2.05 (br d, 2H), 1.85 (m, 1H), 1.69 (m, 4H), 1.29 (m, 2H). M+H=338.

Formula 1 Compound Salt Formation, Example 1

To a flask was charged maleic acid (9.5 g, 81.8 mmol), N-methyl-1-{trans-4-[methyl(7H-pyrrolo[2,3-d]pyrimidin-4-yl)amino]cyclohexyl}methanesulfonamide (Formula 1 compound; 25 g, 74.1 mmol), and water (250 mL). This was heated to about 60° C. and the materials formed a clear solution. The solution was cooled to about 55° C. and seeded with previously isolated maleic acid salt of the Formula 1 compound (25 mg, 0.7 mmol). The reaction was cooled to about 37° C. at a rate of about 1° C. per hour and then to about 5° C. at a rate of about 3° C. per hour. The product was isolated by filtration and washed with water (100 mL). This afforded 30.9 g of white material, N-methyl-1-{trans-4-[methyl(7H-pyrrolo[2,3-d]pyrimidin-4-yl)amino] cyclohexyl}methanesulfonamide, maleate, as the monohydrate, Form B(A). 1H NMR (600 MHz, DMSO-d6) 12.0 (s, 1H), 8.18 (s, 1H), 7.25 (br s, 1H), 6.90 (q, 1H), 6.64 (br s, 1H), 6.19 (s, 2H), 4.55 (br s, 1H), 3.20 (s, 3H), 2.95 (d, 2H), 2.58 (d, 3H), 2.05 (d, 2H), 1.85 (m, 1H), 1.72 (br s, 4H), 1.30 (m, 2H).

Formula 1 Compound Salt Formation, Example 2

To a flask was charged maleic acid (14.45 g, 124.5 mmol), N-methyl-1-{trans-4-[methyl(7H-pyrrolo[2,3-d]pyrimidin-4-yl)amino]cyclohexyl}methanesulfonamide (Formula 1 compound; 40 g, 118.5 mmol), and water (400 mL). This was heated to about 65° C. and the materials formed a clear solution. The solution was cooled to about 50° C. and seeded with previously isolated maleic acid salt of the Formula 1 compound (400 mg, 0.8 mmol). The reaction was cooled to about 40° C. at a rate of about 2° C. per hour and then to about 5° C. at a rate of about 5° C. per hour. The product was isolated by filtration and washed with cold water (160 mL), then dried with air at 42% relative humidity. This afforded 50.0 g of white material, N-methyl-1-{trans-4-[methyl(7H-pyrrolo[2,3-d]pyrimidin-4-yl)amino]cyclohexyl}methanesulfonamide, maleate, as the monohydrate, Form B(A).

Formula 1 Compound Salt Formation, Example 3

To a tank containing N-methyl-1-{trans-4-[methyl(7H-pyrrolo[2,3-d]pyrimidin-4-yl)amino] cyclohexyl}methanesulfonamide (Formula 1 compound) and maleic acid (1.1 eq; 0.378 kg/kg Formula 1 compound) was added about 50° C. to about 65° C. water (10 L/kg) and the mixture stirred at about 55° C. to about 60° C. until the solids dissolved. The solution was clarified into a preheated tank and again stirred at about 55° C. to about 60° C. to obtain a clear solution. The crystallization mixture is cooled to about 45° C. and seeded with previously isolated Form C product. The jacket was adjusted to provide cooling of about 1° C./hour until about 37° C. is reached and then about 3° C./hour to about 0° C. to about 5° C. After a short stir period the product was collected by filtration and washed with cold water (5 L/kg). The product (Form C) was dried with tempered (about 40° C.) low dew-point nitrogen until the water content by Karl Fischer was approximately 4%.

Crystal Forms

Figure 2:
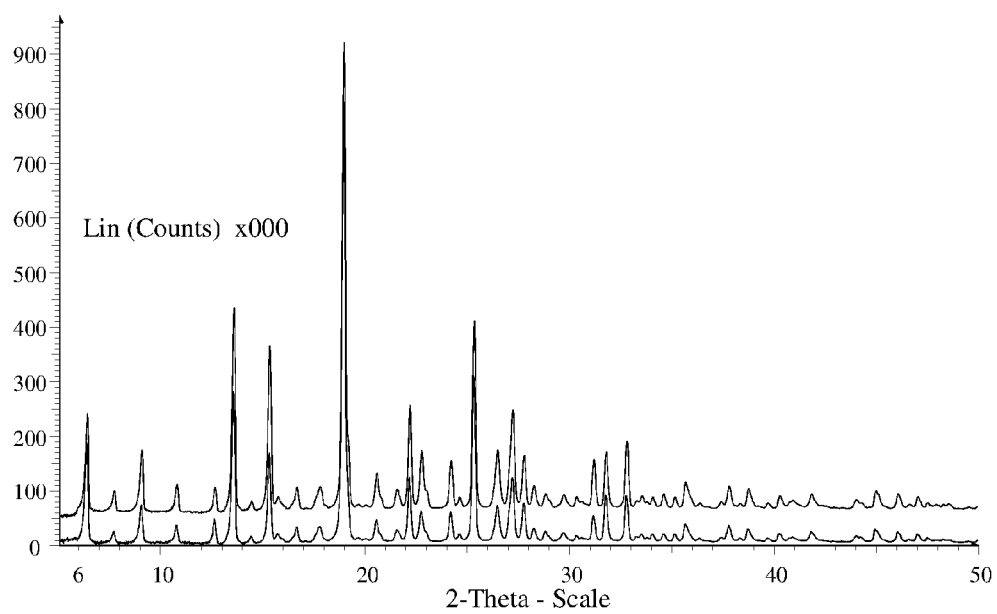
FIG. 2. Depicts an illustrative PXRD pattern of crystalline Form B (reference standard) overlaying Form B(A).
Figure 3:
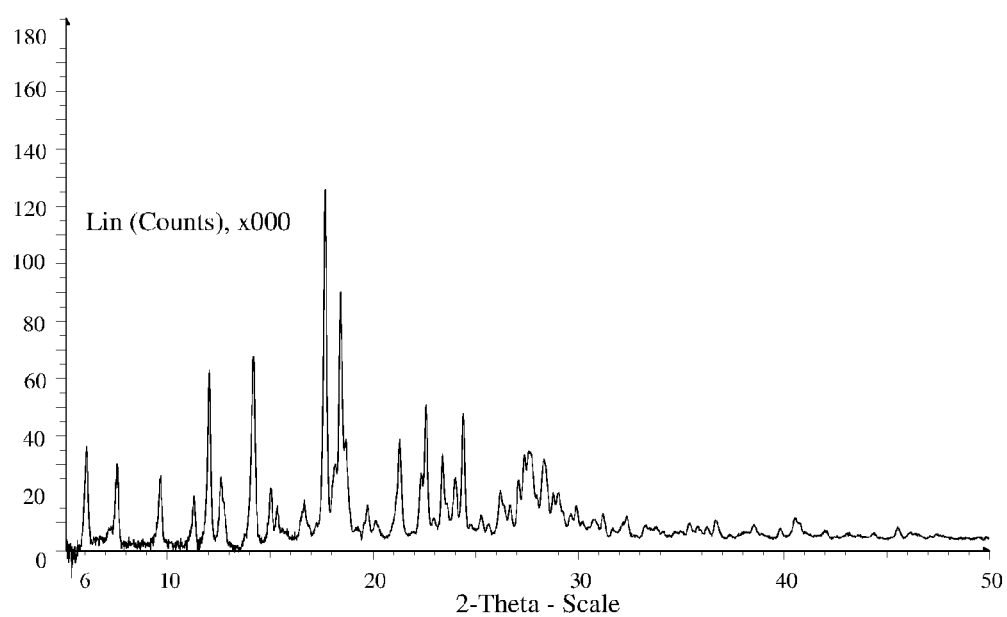
FIG. 3. Depicts an illustrative PXRD pattern of crystalline Form C.

A number of crystal forms of N-methyl-1-{trans-4-[methyl(7H-pyrrolo[2,3-d]pyrimidin-4-yl)amino]-cyclohexyl}methanesulfonamide, maleate, are known and are shown in FIGS. 1-3. Form A was described in U.S. Pat. No. 8,987,283, and is an anhydrate. Form B is a monohydrate. Because the Form A and Form B are chemically different by a molecule of water, they are not polymorphs in the strict sense of polymorphism, so the more general terms, form or crystal form, is used. Form B(A) is predominantly Form B, but may include a small fraction of the anhydrate (Form A). The Form B(A) PXRD of Example 2 is shown in FIG. 1 with peak positions, d-spacings, and 2-theta values in Table 1. The reference standard for Form B(A) is used for quantitating N-methyl-1-{trans-4-[methyl(7H-pyrrolo[2,3-d]pyrimidin-4-yl)amino]-cyclohexyl}methanesulfonamide maleate (Apoquel). The superimposed B(A) reference standard and Example 2 PXRD scans are shown in FIG. 2. Form C is a hydrate form with variable stoichiometry depending on the relative humidity and its PXRD is shown in FIG. 3 with peak positions, d-spacings, and 2-theta values shown in Table 2.

Figure 4:
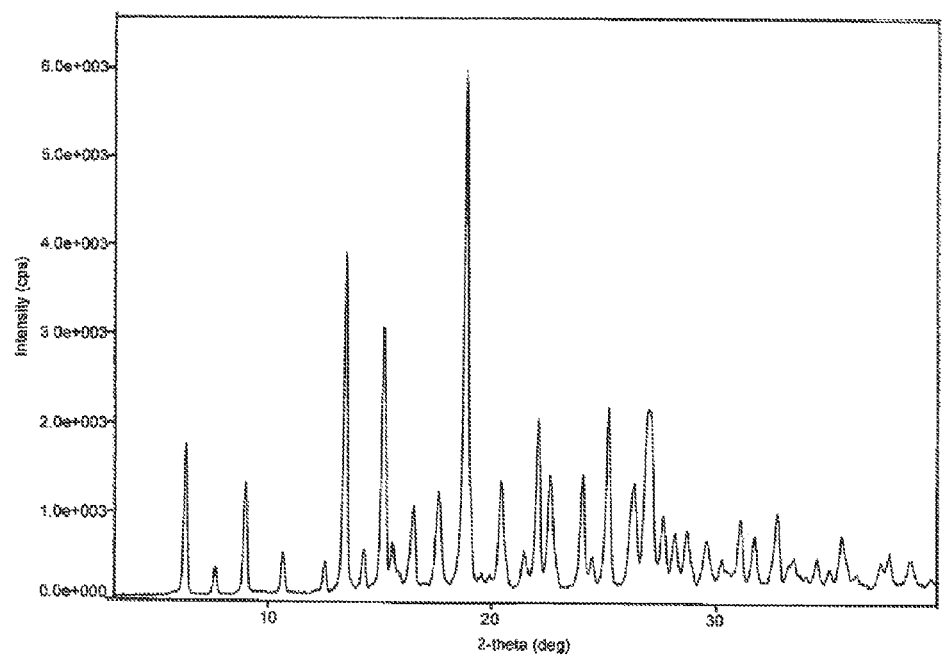
FIG. 4. Comparative PXRD of Crystal Form B(A) of N-methyl-1-{trans-4-[methyl(7H-pyrrolo[2,3-d]pyrimidin-4-yl)amino]-cyclohexyl}methanesulfonamide,maleate

A comparative Form B(A) PXRD pattern and peak positions, d-spacings, and 2-theta values from N-methyl-1-{trans-4-[methyl(7H-pyrrolo[2,3-d]pyrimidin-4-yl)amino]-cyclohexyl}-methanesulfonamide maleate (Lot X) prepared according to processes described in U.S. Pat. No. 8,987,283 and U.S. Pat. No. 6,890,929 are shown in FIG. 4 and Table 3, respectively.

The X-ray diffractograms were obtained using a Bruker AXS [Coventry, UK] Endeavor D4 equipped with a Lynx-Eye detector operated with a fixed slit and a Cu source operated at 40 kV and 40 mA (15 mA-LotX), K2a wavelength 1.5406 angstroms. The diffractogram was obtained in the region of 3 to 50 (40-LotX) degrees two-theta. The step size was 0.020 (0.030-LotX) degrees two-theta, and the acquisition time per step was 0.5 seconds. During acquisition, the sample holder was rotated at 20 rpm. Samples were prepared for analysis by spreading loose solids on zero-background silica wafers in such a fashion as to provide a level surface for the analysis. Data were analyzed in the EVA software package obtained from Bruker AXS.

As will be appreciated by the skilled crystallographer, the relative intensities of the various peaks reported in the Tables and Figures herein may vary due to a number of factors such as orientation effects of crystals in the X-ray beam or the purity of the material being analyzed or the degree of crystallinity of the sample. The PXRD peak positions may also shift for variations in sample height but the peak positions will remain substantially as defined in the Tables. The skilled crystallographer also will appreciate that measurements using a different wavelength will result in different shifts according to the Bragg equation—$n\lambda = 2ci \sin \theta$. Such further PXRD patterns generated by use of alternative wavelengths are considered to be alternative representations of the PXRD patterns of the crystalline materials of the present invention and as such are within the scope of the present invention.

TABLE 1

PXRD Peak Data for Crystal Form B(A) of N-methyl-1-{trans-4-[methyl(7H-pyrrolo[2,3-d]pyrimidin-4-yl)amino]-cyclohexyl}methanesulfonamide, maleate

| Peak | d-spacing (A °) | 2-theta ° |
| --- | --- | --- |
| 1 | 13.97 | 6.32 |
| 2 | 9.81 | 9.01 |
| 3 | 6.54 | 13.52 |
| 4 | 5.79 | 15.28 |
| 5 | 4.69 | 18.92 |
| 6 | 4.01 | 22.16 |
| 7 | 3.91 | 22.73 |
| 8 | 3.68 | 24.18 |
| 9 | 3.52 | 25.30 |
| 10 | 3.36 | 26.47 |
| 11 | 3.28 | 27.20 |
| 12 | 3.21 | 27.76 |
| 13 | 2.81 | 31.79 |
| 14 | 2.73 | 32.80 |

TABLE 2

PXRD Peak Data for Crystal Form C of N-methyl-1-{trans-4-[methyl(7H-pyrrolo[2,3-d]pyrimidin-4-yl)amino]-cyclohexyl}methanesulfonamide, maleate

| Peak | d-spacing (A °) | 2-theta ° |
| --- | --- | --- |
| 1 | 14.71 | 6.01 |
| 2 | 11.79 | 7.49 |
| 3 | 9.20 | 9.60 |
| 4 | 7.38 | 11.98 |
| 5 | 7.04 | 12.57 |
| 6 | 6.26 | 14.15 |
| 7 | 5.03 | 17.64 |
| 8 | 4.90 | 18.11 |
| 9 | 4.82 | 18.40 |
| 10 | 4.75 | 18.67 |
| 11 | 4.17 | 21.27 |
| 12 | 3.98 | 22.33 |
| 13 | 3.94 | 22.55 |
| 14 | 3.80 | 23.38 |
| 15 | 3.71 | 23.99 |
| 16 | 3.65 | 24.37 |
| 17 | 3.26 | 27.36 |
| 18 | 3.23 | 27.62 |
| 19 | 3.15 | 28.32 |

TABLE 3

Comparative PXRD Peak Data for Crystal Form B(A) of N-methyl-1-{trans-4-[methyl(7H-pyrrolo[2,3-d]pyrimidin-4-yl)amino]-cyclohexyl}methanesulfonamide, maleate

| Peak | d-spacing (A °) | 2-theta ° |
| --- | --- | --- |
| 1 | 14.07 | 6.28 |
| 2 | 9.85 | 8.97 |
| 3 | 6.56 | 13.49 |
| 4 | 5.82 | 15.21 |
| 5 | 4.69 | 18.89 |
| 6 | 4.02 | 22.11 |
| 7 | 3.93 | 22.62 |
| 8 | 3.69 | 24.12 |
| 9 | 3.52 | 25.25 |
| 10 | 3.38 | 26.36 |
| 11 | 3.29 | 27.12 |
| 12 | 3.22 | 27.67 |
| 13 | 2.82 | 31.71 |
| 14 | 2.73 | 32.74 |

What is claimed is:

1. A process for preparing a compound of Formula 1

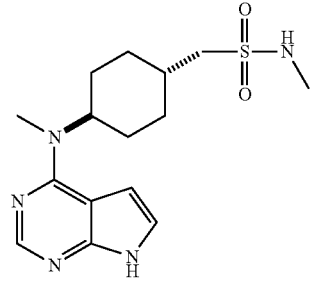

(1)

or a veterinary acceptable salt thereof, comprising
(a) reacting the compound, trans-4-((methylamino)cyclohexyl)methanesulfonic acid with the 7H-pyrrolo[2,3-d]pyrimidine D1 analog in water or an aqueous organic solvent with a base at a reaction temperature of about 60° C. to about 105° C. to prepare the sulfonate salt, wherein W is Cl, F, Br, I, O-triflate, O-mesyl, or O-tosyl,

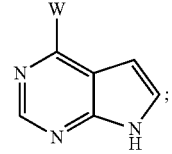

(D1)

(b) conversion of the sulfonate salt, trans-4-(methyl(7H-pyrrolo[2,3-d]pyrimidin-4-yl)amino)cyclohexyl)methane sulfonic acid, potassium salt, to the sulfonyl chloride intermediate,((trans)-4-(methyl(7H-pyrrolo[2,3-d]pyrimidin-4-yl)amino)cyclohexyl)-methanesulfonyl chloride, in an organic solvent; and (c) conversion of the sulfonyl chloride intermediate to the Formula 1 compound by reacting the sulfonyl chloride intermediate with a cold aqueous solution of methylamine.

2. The process of claim 1, Step (a), wherein the 7H-pyrrolo[2,3-d]pyrimidine D1 analog is 4-chloro-7H-pyrrolo[2,3-d]pyrimidine and the reaction occurs in water or in an aqueous organic solvent that is 5% N-methylpyrrolidone or sulfolane, and the base is potassium carbonate and the reaction temperature is about 98° C. for about 12 hours.

3. The process of claim 1, Step (b), wherein the conversion of the sulfonate salt to the sulfonyl chloride intermediate is prepared by reacting the sulfonate salt with oxalyl chloride, thionyl chloride, or phosphoryl chloride in an organic solvent.

4. The process of claim 3 wherein the organic solvent comprises acetonitrile or tetrahydrofuran, and wherein the reaction temperature is in the range of about 0° C. to about 20° C.

5. The process of claim 4 wherein the organic solvent further comprises dimethylacetamide, diisopropylformamide or dimethylformamide.

6. The process of claim 5 wherein the organic solvent comprises tetrahydrofuran and diisopropylformamide.

7. The process of claim 1 wherein the aqueous methylamine is about 40% and is at about −10° C.

8. The process of claim 7 further comprising the addition of water to the reactants after addition of the sulfonyl chloride intermediate to the cold methylamine solution.

9. The process of claim 8 wherein the reactants are slowly heated to reflux, and then the solvents are distilled off at a temperature of about 65° C. to about 75° C., the resultant solids are cooled to about 35° C., then the solids are filtered, washed with water, filtered and dried.

10. The process of claim 1 wherein trans-4-((methyl-amino)cyclohexyl)methane sulfonic acid is reacted with the 7H-pyrrolo[2,3-d]pyrimidine D1 analog, 4-chloro-7H-pyrrolo[2,3-d]pyrimidine with a base which is potassium carbonate in water at a reaction temperature of about 98° C. to prepare the sulfonate salt; conversion of the sulfonate salt to the sulfonyl chloride intermediate in an organic solvent which is THF; and conversion of the sulfonyl chloride intermediate to the Formula 1 compound by reacting the sulfonyl chloride intermediate with a cold aqueous solution of methylamine.

11. The process of claim 10 wherein the about 98° C. reaction proceeds for about 12 hours and wherein the organic solvent further comprises DIPF.

12. The process of claim 11 wherein oxalyl chloride, thionyl chloride, or phosphoryl chloride is added to the sulfonate salt to convert the sulfonate salt to the sulfonyl chloride intermediate and the reaction temperature is about 10° C.

13. The process of claim 12 wherein the methylamine is about 40% methylamine at about −10° C.

14. The process of claim 13, further comprising the addition of water to the reactants after addition of the methylamine and slowly heating the reactants to reflux.

15. The process of claim 14, further comprising the distilling off of solvents at a temperature of about 65° C. to about 75° C., cooling the resultant solids to about 35° C., isolating the solids by filtration, washing the solids with water, filtering and drying the solids.

16. A process for preparing the compound, Intermediate C,

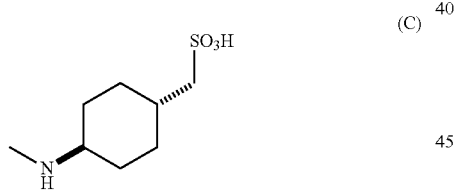

(C)

comprising the steps of:
a) reacting 4-bromobenzylbromide with a sodium sulfite salt in water or an aqueous solvent comprising about 10-30% acetonitrile at about 80° C., and isolating the solids, Intermediate A, by filtration, wherein Intermediate A is sodium (4-bromophenyl)methanesulfonate;
b) reacting the solids, Intermediate A, in aqueous 10% to 25% methylamine and a CuBr catalyst at a temperature of at least about 50° C. for about 16 hours, then cooling the reactants to about 65° C., removal of residual copper, adding water and adjusting the pH to 3.2 with concentrated HCl, cooling the reaction to about 15° C., and isolating the solids, Intermediate B, by filtration, wherein Intermediate B is (4-(methylamino)phenyl) methanesulfonic acid;
c) reacting the solids, Intermediate B, in an aqueous organic solvent containing about 25% methanol with a palladium catalyst and hydrogen at about 50° C. to about 80° C. for about 14 hours to about 18 hours; and
d) concentrating the volume from the previous reaction, adding an alcohol and heating to about 45° C., then cooling the reaction to about 0° C. over about 4 hours, and isolating the solids, Intermediate C, by filtration, and washing with an alcohol.

17. The process of claim 16, Step (a) wherein the acetonitrile is about 15%; and Step (b), wherein the aqueous methylamine is about 17% and the CuBr catalyst is about 2 mol % and temperature of at least about 50° C. is about 90° C., and wherein the residual copper is removed by addition of a citric acid solution.

18. The process of claim 16, Step (c), wherein the palladium catalyst is a Pd(0) catalyst and the hydrogen is hydrogen gas at about 70° C. for about 16 hours.

19. The process of claim 16, Step (d) wherein the alcohol is ethanol.

20. A compound selected from the group consisting of:
(4-(methylamino)phenyl)methanesulfonic acid;
trans-4-((methylamino)cyclohexyl)methanesulfonic acid;
trans-4-(methyl(7H-pyrrolo[2,3-d]pyrimidin-4-yl)amino) cyclohexyl)methane sulfonic acid, potassium salt;
trans-4-(methyl(7H-pyrrolo[2,3-d]pyrimidin-4-yl)amino) cyclohexyl)methane sulfonic acid, sodium salt; and
((trans)-4-(methyl(7H-pyrrolo[2,3-d]pyrimidin-4-yl) amino)cyclohexyl)-methanesulfonyl chloride.

* * * * *

UNITED STATES PATENT AND TRADEMARK OFFICE
CERTIFICATE OF CORRECTION

PATENT NO. : 9,926,327 B2
APPLICATION NO. : 15/426292
DATED : March 27, 2018
INVENTOR(S) : Stuk et al.

Page 1 of 1

It is certified that error appears in the above-identified patent and that said Letters Patent is hereby corrected as shown below:

Scheme 1, Column 17, Lines 40-60 is incorrect. The correct Scheme 1 is presented herewith.

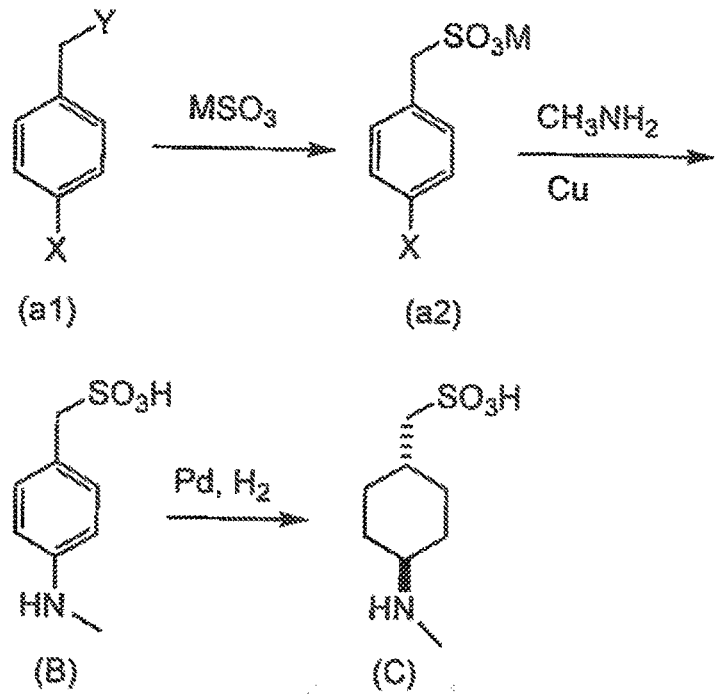

Signed and Sealed this
Eighth Day of May, 2018

Andrei Iancu
*Director of the United States Patent and Trademark Office*